(12) United States Patent
Corbett et al.

(10) Patent No.: US 8,080,410 B2
(45) Date of Patent: Dec. 20, 2011

(54) CENTRIFUGAL DEVICE AND METHOD FOR PERFORMING BINDING ASSAYS

(75) Inventors: John Michael Corbett, Sanctuary Cove (AU); John Michael Corbett, Jr., Bellevue Hill (AU)

(73) Assignee: Corbett Life Science Pty Ltd, New South Wales (NZ)

( * ) Notice: Subject to any disclaimer, the term of this patent is extended or adjusted under 35 U.S.C. 154(b) by 858 days.

(21) Appl. No.: 10/535,666

(22) PCT Filed: Nov. 20, 2003

(86) PCT No.: PCT/AU03/01552
§ 371 (c)(1),
(2), (4) Date: Apr. 19, 2006

(87) PCT Pub. No.: WO2004/046719
PCT Pub. Date: Jun. 3, 2004

(65) Prior Publication Data
US 2006/0223061 A1  Oct. 5, 2006

(30) Foreign Application Priority Data
Nov. 20, 2002  (AU) ................................. 2002952797

(51) Int. Cl.
*C12M 1/34* (2006.01)
*C12M 3/00* (2006.01)
(52) U.S. Cl. ............... 435/288.4; 435/283.1; 435/287.2; 435/288.3; 422/82.05; 422/82.08; 422/82.09

(58) Field of Classification Search ............... 435/283.1, 435/287.2, 288.3, 288.1; 422/82.05, 82.08, 422/82.09
See application file for complete search history.

(56) References Cited

U.S. PATENT DOCUMENTS

| | | | |
|---|---|---|---|
| 3,763,374 A | | 10/1973 | Tiffany et al. |
| 6,093,370 A | * | 7/2000 | Yasuda et al. ................ 422/68.1 |
| 6,210,885 B1 | * | 4/2001 | Gjerde et al. ..................... 435/6 |
| 6,236,454 B1 | * | 5/2001 | Almogy ..................... 356/237.3 |
| 7,141,416 B2 | * | 11/2006 | Krutzik ....................... 435/288.5 |
| 2002/0098528 A1 | * | 7/2002 | Gordon et al. ............... 435/7.21 |
| 2002/0168652 A1 | * | 11/2002 | Werner et al. ..................... 435/6 |
| 2002/0177144 A1 | * | 11/2002 | Remacle et al. ................... 435/6 |
| 2003/0054376 A1 | * | 3/2003 | Mullis et al. ...................... 435/6 |

FOREIGN PATENT DOCUMENTS

| | | |
|---|---|---|
| WO | WO 95/31731 | 11/1995 |
| WO | WO 01/66555 | 9/2001 |
| WO | WO 01/67102 | 9/2001 |
| WO | WO 02/39125 | 5/2002 |

* cited by examiner

*Primary Examiner* — Melanie J Yu
(74) *Attorney, Agent, or Firm* — Baker, Donelson, Bearman, Caldwell & Berkowitz, PC

(57) ABSTRACT

The invention relates to a device for performing binding assays. In particular, the invention relates to a centrifugal device for performing such assays. The invention also relates to a method of performing binding assays involving antigen-antibody binding, nucleic acid hybridization, or receptor-ligand interaction.

14 Claims, 1 Drawing Sheet

CENTRIFUGAL DEVICE AND METHOD FOR PERFORMING BINDING ASSAYS

The present application is based on International Application PCT/AU2003/001552, filed Nov. 20, 2003, which application is incorporated herein by reference in its entirety.

TECHNICAL FIELD

The invention the subject of this application relates to a device for performing binding assays. In particular, the invention relate to a centrifugal device for performing such assays. The invention also relates to a method of performing binding assays involving antigen-antibody binding, nucleic acid hybridization, or receptor-ligand interaction.

BACKGROUND ART

A fundamental aspect of research in the biological and medical sciences is the measurement of the binding of one chemical entity to another chemical entity. Such measurements are usually referred to as binding assays and include the measurement of the binding of an antigen to an antibody or vice versa, the bending of one nucleic acid to another nucleic acid such as in a hybridization reaction, and the binding of a ligand such as a hormone or other effector molecule to its receptor.

There are numerous techniques available for performing binding assays with the technique employed for a particular assay usually being dictated by the types of molecules involved in the interaction. In general, however, one of the partners in the interaction is bound to a solid support such as a membrane or the walls of wells in microtitre plates. Many of the known techniques are automated and are adapted for the simultaneous assaying of multiple samples.

While known techniques permit the efficient performance of numerous assays in a given period, the techniques have limitations. The most serious limitation is that a particular technique and the apparatus associated therewith can usually only be used for a single binding assay. Many of the techniques further suffer from the complication that multiple steps are involved in which reagents have to be sequentially added and removed.

It would therefore be desirable to have available apparatus that can be used for performing a variety of binding assays—even simultaneously—under variable conditions and by which the assays can be done with avoidance of the multiplicity of steps necessary in known procedures.

The object of the invention is to provide such an apparatus and methods utilizing that apparatus.

SUMMARY OF THE INVENTION

In a first embodiment of the invention, there is provided a device for measuring the binding of a first partner in an interaction to a second partner in said interaction, said device comprising:
a) an opaque temperature-controlled chamber having a rotor therein, said rotor having at or near the periphery thereof at least one radially positioned transparent reaction well, said reaction well having on an upper surface thereof an aperture for the addition of reagents thereto, said reaction well further including on an internal surface thereof at the end closest the axis of said rotor at least one attachment zone for said second interaction partner;
b) a system for detecting light emitted or absorbed by said first interaction partner or an indicator molecule bound thereto; and
c) means for controlling the temperature of said chamber and the operation of said rotor.

In a second embodiment, the invention provides a method of measuring the binding of a first partner in an interaction to a second partner in said interaction, said method comprising the steps of:
a) delivering a quantity of second interaction partner to a reaction well of a device according to the first embodiment for attachment of said second interaction partner to an attachment zone of said reaction well;
b) combining a quantity of first interaction partner with said second interaction partner in said reaction well and incubating said mixture at a temperature and for a time to allow binding of said first interaction partner to said second interaction partner;
c) rotating said device rotor at a speed which displaces the mixture formed in step (b) away from said attachment zone; and
d) measuring the amount of said first interaction partner bound to said second interaction partner via the fluorescence or absorbance of said first interaction partner or an indicator molecule bound thereto.

Other embodiments of the invention will become apparent from a reading of the detailed description below.

DETAILED DESCRIPTION OF THE INVENTION

Figure 1:
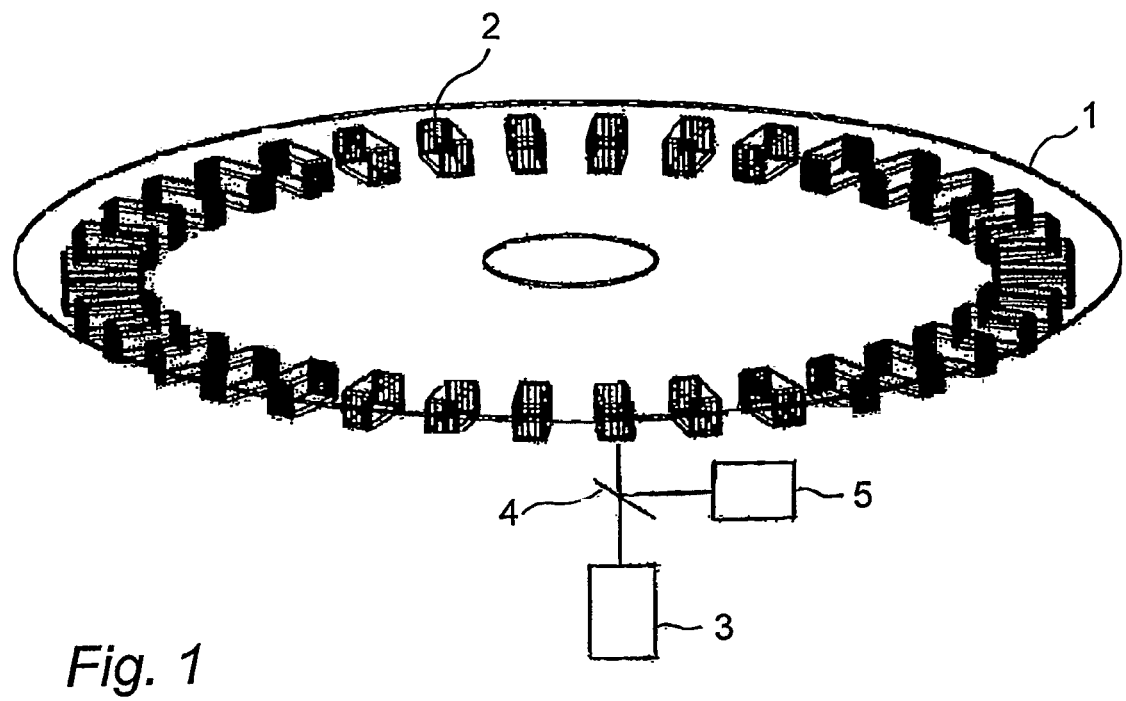
FIG. 1 is a semi schematic representation of a rotor of a device according to the invention with detail of a optical detection system included.

The term "interaction" is used herein to denote the binding of any molecule (the first interaction partner) to another molecule (the second interaction partner) where the interaction may be a naturally occurring interaction or the binding of a synthetic molecule to a target molecule.

The interaction partners can be any pair of molecules in which a first molecule can bind to the second molecule. The term interaction partner therefore includes, but is not limited to, the following pairs of molecules:

| First Interaction Partner | Second Interaction Partner |
| --- | --- |
| Antibody | Antigen |
| Antigen | Antibody |
| Enzyme | Substrate |
| Oligopeptide | Protein (for example, an enzyme or receptor) |
| Hormone | Receptor |
| Effector molecule | Receptor |
| Nucleic Acid (RNA or DNA) | Nucleic acid (RNA or DNA) |
| Oligonucleotide | Nucleic acid (RNA or DNA) |
| Synthetic organic compound | Protein (for example, an enzyme or receptor) |

The terms "comprise" and variants of the term such as "comprises" or "comprising" are used herein to denote the inclusion of a stated integer or stated integers but not to exclude any other integer or any other integers, unless in the context or usage an exclusive interpretation of the term is required.

With regard to the first embodiment of the invention as define above, the device chamber can be any suitable, typically insulated, container for the rotor and other device components. The chamber advantageously has a lid or sealable opening to allow loading of reaction wells. The chamber must be opaque—that is, impermeable to light—to allow accurate and sensitive measurement of the second interaction partner molecule or indicator molecule.

The temperature control of the device chamber is effected by providing a heater linked to a temperature sensor so that a set temperature can be maintained. Typically, heating is by a heater located within the chamber with circulation of heated air within the chamber aided by a fan. Alternatively, heated air can be supplied to the chamber from a port or ports in a chamber wall. Heating of the chamber can also be by infrared radiation.

Temperature control can also include a cooling system. For example, air supply to the chamber can be provided wherein the air is either at ambient temperature or less than ambient by passage through or over a cooling means. The temperature sensor referred to above is advantageously linked to the cooling system.

The device rotor is typically a flat disc of a plastic or metal material having reaction wells fitted therein. The reaction wells can be removable or the entire rotor with reaction wells can be a disposable item. The rotor of devices according to the invention advantageously comprise a plurality of reaction wells. The number of wells will depend on the configuration of the device but a typical range is 1 to 96 wells.

Reaction wells can be formed from any suitable transparent material such as polypropelene or polycarbonate. The wells can be cylindrical, rectangular prisms, or any other suitable shape provided that the well is of sufficient length to provide an area for the at least one attachment zone and an area into which the solution or solutions via which the interaction partners were applied can be displaced by centrifugal force.

In some embodiments, the reaction wells can be angled upwards toward the periphery of the rotor. This allow solution to migrate back to the at least one attachment zone once rotor speed has been sufficiently reduced. The function of such migration will be explained below. Transitory vibration of the rotor can also be used to effect migration of solution in a reaction well and in such instances the well does not have to be tilted and can be horizontal.

Attachment zones are typically provided by appropriately treating the surface, spotting the second interaction partner onto the attachment zone with a pin or ink-jet, and drying the spotted component. Alternatively, a magnet can be provided beneath the desired area of a reaction well. The second interaction partner is linked to a magnetic particle which is held in the attachment zone by the magnet. Attachment zones typically have a diameter, if a circular zone, of 50 μm to 3 mm. A particular reaction well can have a plurality of attachment zones allowing different second interaction partners to be delivered to that well if desired.

The rotor drive means can be any drive means used for rotor devices in scientific equipment. For example, the drive means can be direct-coupled AC motor, a DC motor, or an AC motor that drives the rotor via a gearbox or pulleys or the like. Preferably, the drive means is a direct-coupled AC motor, DC motor or stepper motor with the motor external to the chamber.

The detection system comprises a light source and a detector. These components can be any of the light sources and detectors know to those of skill in the art. For example, the light source can be an LED, a laser light source or a halogen lamp, with an appropriate filter to provide light of an appropriate wavelength for:

a) excitation of any fluorophore associated with the first interaction partner (by associated it is meant that the fluorophore is directly linked to the first interaction partner molecule or is linked to an indicator molecule); or b) absorbance by the first interaction partner or indicator molecule.

The detector will be suitable for the measurement of emitted fluorescence or absorbance. Detection systems advantageously include both types of detectors to give the device greater versatility in the types of binding assays that can be performed.

A device according to the invention can have associated therewith a computer for controlling such operations as:

Rotor speed;

Chamber temperature;

Time and temperature for annealing and polymerization steps when the binding assay is an hybridization;

Rotor braking;

Vibration of the rotor; and

Processing of data generated by the detection system.

A device that can be suitably adapted for use in the present invention is that described in International Application No. PCT/AU98/00277 (Publication No. WO 98/49340) the entire content of which is incorporated herein by cross reference.

With regard to the second embodiment of the invention, a method of performing a binding assay utilizing the device of the first embodiment, the quantities of first and second interaction partners are advantageously delivered as solutions which can contain other components such as buffers, salts, DNA or RNA polymerization reagents including a polymerase, or a blocking reagent if necessary. Solutions of interaction partners can be delivered by any of the methods known to those of skill in the art.

Temperatures and incubation times will be in accordance with the particular binding assay being performed and those parameters will be known to those of skill in the art. For example, hybridization reactions can be performed as described in *Molecular Cloning: A Laboratory Manual*, Second Edition (J. Sambrook et al., ed's), Cold Spring Harbour Laboratory Press, 1989. For performing a polymerase chain reaction, typical reaction mixtures and conditions are described, for example, in standard texts such as *PCR: a Practical Approach* (M. J. McPherson et al., ed's), IRL Press, Oxford, England, 1991, and numerous brochures provided by suppliers of amplification reagents and consumables. The entire content of the foregoing publications is incorporated herein by cross reference.

Binding of the first interaction partner to the second interaction partner can be done with the rotor spinning. The solution containing the mixture of interaction partners can usually be spun at a speed of less than 500 rpm while retaining the solution at the attachment zone. A speed of greater than 500 rpm is usually sufficient to displace solution—and hence any unbound first binding partner—away from the attachment zone. The bound first interaction partner is then measured by way of the detection system.

To allow measurement of bound first interaction partner, the partner has:

An inherent absorbance (which is different, if necessary, at the selected wavelength to the absorbance of other components of the binding assay); or Has linked thereto a fluorescent or absorbent group.

Suitable fluorescent and absorbent groups will be known to those of skill in the art. Typical fluorophores include those abbreviated as FAM, JOE, ROX, TAMRA, Cy5, Cy3, Cy5.5, and VIC. Typical absorbent groups are Dabcyl and BH quenchers.

Alternatively, the bound first interaction partner can be measured by allowing an indicator molecule to bind thereto. This can be done as a further step after unbound first interaction partner is displaced form the attachment zone. Excess indicator molecule is similarly removed by centrifugal force after a sufficient period has been allowed at a suitable temperature for binding of the indicator molecule to the bound first interaction partner.

In instances where the first and second interaction partners form a DNA duplex or a DNA duplex is formed as a PCR product, an intercalating dye can be used to detect the duplex. Such dyes will be known to those of skill in the art. A particularly preferred dye is Sybr green.

The indicator molecule can be any molecule that is fluorescent or absorbs at an appropriate wavelength and which binds to the first interaction partner. Typically, the indicator molecule is an appropriately derivatised antibody that is specific for the first interaction partner.

Absorbance or fluorescence is measured with the rotor spinning, typically at a speed of at least 500 rpm at which speed the mixture will move away from the attachment zone. Data capture is controlled so that each attachment zone that passes over or under the detector is independently measured. Multiple detectors can be provided for use with reaction wells that include multiple attachment zones. Alternatively, a single detector can be used, with appropriate control, to scan all attachment zones.

A device according to the invention will now be described with reference to the accompanying figures. FIG. 1 shows rotor 1 of a device having a plurality of reaction wells mounted thereto, one of which wells is item 2. A laser or diode 3 is provided as a light source, light from which is directed through a beam splitter or dichroic mirror 4. Emitted fluorescence or absorbed light is measured by detector 5.

Figure 2:
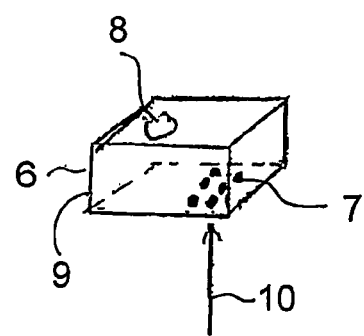
FIG. 2 is a representation of one of the reaction wells of a rotor of a device according to the invention.

FIG. 2 shows a reaction well 6 which in this instance is a rectangular prism fabricated from polypropylene. Well 6 has at its end which is closest the axis of the rotor when the well is in situ a plurality of attachment zones one of which is item 7. The upper surface of well 6 has a loading port 8. In use, after reagents have been added to the well, the solution thereof is displaced to end 9 of the well by centrifugal force through rotation of the rotor holding well 6. Bound first interaction partner is then detected as schematically represented by arrow 10.

Examples of binding assays that can be performed using the device and method of the invention will now be given.

Realtime Detection of PCR Products

A probe or a primer is bound at the attachment site, and PCR performed in the vessel. The following are done during PCR cycling:
1) After each cycle of PCR at high rotor speed (greater than 500 rpm) the rotor is slowed so that the reaction mix covers the attachment zone (this is done at the annealing temperature of the primer/probe to the PCR product).
2) After a specified annealing time, the rotor speed is increased to remove the PCR mix from the attachment zone.
3) Fluorescence readings are taken at the attachment zone.
4) The previous steps are repeated.

Determination of Probe Melting Temperature

A primer or probe is bound to an attachment zone of a reaction well of a device according to the invention. A PCR reaction mix is added to the vessel, that includes at least one fluorescently-labeled primer. The rotor is spun at high speed to ensure no contact with the attachment zone and then the vessel cycled to perform PCR amplification. After amplification, the rotor is slowed to allow the PCR mix to come into contact with the attachment zone, so that the PCR product will hybridize specifically to the immobilized probe or primer. The temperature is reduced to below the expected melt temperature during this step to allow hybridization to occur. The rotor is then spun at high speed, the fluorescent signal at the attachment zone is sampled and the temperature of the chamber increased slowly, typically at 0.20° C. per second. The fluorescent signal captured will confirm the melt temperature of the primer/probe and PCR product.

Reference was made above to vibration of the rotor to move solution back over the attachment zone. This can also be achieved through use of a tilted reaction well. On sufficient slowing of the rotor, solution moves from an upward position at the distal end (relative to the axis of the rotor) to a lower portion over the attachment zone area of the reaction well. Rotor vibration is thus not needed in this embodiment of the device.

Determination of Antigen Levels in a Sample

An antibody specific for the antigen of interest is bound at an attachment zone of a reaction well. A sample containing an unknown amount of antigen is then allowed to react with the antibody. Solvent is removed by centrifugation and a solution containing an antibody to the antigen is applied to the attachment zone. This antibody may be the same or different to the antibody referred to above but is fluorescently labeled. Excess second antibody is then removed by centrifugation and the amount of antigen measured by fluorescence.

SNP Detection Using PCR

Synthetic probes for the mutated and wild type sequences are bound to separate attachment zones of a reaction well. The well is then loaded with a reaction mixture containing a DNA sample and a PCR master mix. The forward primer is labeled with a fluorophore. After each PCR cycle at the annealing temperature, the rotor speed is reduced and the reaction mixture allowed to overlay the immobilised probes. The rotor speed is then increased to displace reaction mixture and the fluorescence of the DNA retained at the attachment zones measured. An increase in fluorescence indicates amplification of either mutant, wild-type, or both DNAs.

Alternatively, a forward primer that is complementary to a portion of the mutated DNA is labeled with a fluorophore, for example FAM. A forward primer that is complementary to a portion of the wild-type sequence is labeled with a different fluorophore, JOE for example. A probe that is homologous to both the mutation and wild-type PCR products is bound at an attachment zone of a reaction well. By measuring the JOE to FAM ratio of PCR product hybridized with the probe the genotype can be determined.

It will be appreciated that many changes can be made to the device and method of use as exemplified above without departing from the broad ambit and scope of the invention.

The invention claimed is:

1. A method of measuring the binding of a first partner in an interaction to a second partner in said interaction, wherein said interaction partners are molecular entities, said method comprising the steps of
   a) delivering a quantity of said second interaction partner to a reaction well of a device for attachment of said second interaction partner to an attachment zone of said reaction well, wherein said device comprises
      i. an opaque temperature-controlled chamber having a centrifuge rotor therein, said rotor having at or near the periphery of the rotor and attached thereto at least one radially positioned transparent reaction well, said reaction well having on an upper surface thereof an aperture for the addition of reagents to the reaction well, said reaction well further including on an internal surface thereof at the end closest the axis of said rotor at least one attachment zone for said second interaction partner and said well having a sufficient length to provide an area for the at least one attachment zone and an area positioned at the end of the well into which the solution or solutions via which the second interaction partner were applied can be displaced by centrifugal force;
    ii. a system for detecting light emitted or absorbed by said first interaction partner or an indicator molecule bound thereto; and
    iii. means for controlling the temperature of said chamber and the operation of said rotor;
b) adding a solution comprising a quantity of said first interaction partner to said attachment zone and incubating at a temperature and for a time sufficient to allow binding of said first interaction partner to said second interaction partner;
c) rotating said device rotor at a speed sufficient to displace the solution comprising unbound first interaction partner from said attachment zone; and
d) measuring the amount of said first interaction partner bound to said second interaction partner via the fluorescence or absorbance of said first interaction partner or an indicator molecule bound thereto.

2. The method of claim 1, wherein said first and second interaction partners are respectively selected from the group consisting of the following combinations: an antibody and an antigen; an antigen and an antibody; an enzyme and a substrate; an oligopeptide and a protein; a hormone and a receptor; an effector molecule and a receptor; a nucleic acid and a nucleic acid; an oligonucleotide and a nucleic acid; and, a synthetic organic compound and a protein.

3. The method of claim 1, wherein said first and second interaction partners are delivered as solutions containing other components selected from the group consisting of buffers, salts, DNA or RNA polymerization reagents including a polymerase, and a blocking reagent.

4. The method of claim 1, wherein step (b) is carried out with the rotor rotating at a speed of up to 500 rpm.

5. The method of claim 1, wherein step (c) is carried out with the rotor totaling at a speed of greater than 500 rpm.

6. The method of claim 1, wherein said first interaction partner has a fluorophore bound thereto selected from the group consisting of FAM, JOE, ROX, TAMRA, Cy5, Cy3, Cy5.5, and VIC.

7. The method of claim 1, wherein said first interaction partner has a Dabcyl or BH quencher absorbent group bound thereto.

8. The method of claim 1, wherein said indicator molecule is an intercalating dye.

9. The method of claim 8, wherein said intercalating dye is Sybr green.

10. The method of claim 1, wherein said the indicator molecule is a derivatised antibody.

11. The method of claim 1, wherein in step (d) said absorbance or fluorescence is measured with the rotor rotating at a speed of at least 500 rpm.

12. The method of claim 1, wherein said at least one reaction well has multiple attachment zones and measurement of the amount of said that interaction partner bound to said second interaction partner via the fluorescence or absorbance of said first interaction partner or an indicator molecule bound thereto is by way of multiple detectors.

13. The method of claim 1, wherein the temperature control of said chamber is effected by a heater linked to a temperature sensor.

14. The method of claim 13, wherein the temperature control of said chamber is further effected by a cooling system.

* * * * *